United States Patent [19]

Capecchi et al.

[11] Patent Number: 5,489,300
[45] Date of Patent: Feb. 6, 1996

[54] SURGICAL METHOD FOR IMPLANTING A CORNEAL IMPLANT

[75] Inventors: John T. Capecchi, Oakdale, Minn.; Carl Franzblau, Newton, Mass.; Donald F. Gibbons, North Oaks, Minn.; William B. Isaacson, Hudson, Wis.; Manley R. Johnston; Randall L. Knoll, both of Mahtomedi, Minn.; Howard M. Leibowitz, Weston; Vickery Trinkaus-Randall, Maynard, both of Mass.

[73] Assignee: Minnesota Mining and Manufacturing Co., St. Paul, Minn.

[21] Appl. No.: 82,261

[22] Filed: Jun. 24, 1993

Related U.S. Application Data

[60] Continuation of Ser. No. 783,618, Oct. 25, 1991, abandoned, which is a division of Ser. No. 163,383, Mar. 2, 1988, Pat. No. 5,108,428.

[51] Int. Cl.⁶ ........................................... A61F 2/14
[52] U.S. Cl. .......................................... 623/5; 623/6
[58] Field of Search ........................... 623/5, 6, 11, 12, 623/16, 66

[56] References Cited

U.S. PATENT DOCUMENTS

| | | |
|---|---|---|
| 2,714,721 | 8/1955 | Stone, Jr. . |
| 4,118,531 | 10/1978 | Hauser . |
| 4,418,691 | 10/1983 | Yannas et al. . |
| 4,470,159 | 9/1984 | Peyman . |
| 4,475,972 | 10/1994 | Wong . |
| 4,485,096 | 11/1984 | Bell . |
| 4,496,349 | 1/1985 | Cosentino . |
| 4,528,325 | 7/1985 | Ofstead . |
| 4,546,500 | 10/1985 | Bell . |
| 4,563,779 | 1/1986 | Kelman . |
| 4,565,784 | 1/1986 | Franzblau et al. . |
| 4,586,929 | 5/1986 | Binder . |
| 4,604,346 | 8/1986 | Bell et al. . |
| 4,612,012 | 9/1986 | White . |
| 4,618,649 | 10/1986 | Ofstead . |
| 4,673,539 | 6/1987 | Hammer et al. . |
| 4,676,790 | 6/1987 | Kern . |
| 4,715,858 | 12/1987 | Lindstrom .................... 623/5 |
| 4,772,283 | 9/1988 | White . |
| 4,865,601 | 9/1989 | Caldwell et al. . |
| 4,911,720 | 3/1990 | Collier . |
| 4,994,081 | 2/1991 | Civerchia et al. ............. 623/5 |

FOREIGN PATENT DOCUMENTS

| | | | |
|---|---|---|---|
| 0137686 | 4/1985 | European Pat. Off. ......... 623/5 |
| 2705234 | 2/1987 | Germany . |
| 0890032 | 1/1989 | WIPO . |
| 8900032 | 1/1989 | WIPO ........................ 623/5 |

OTHER PUBLICATIONS

Beahan, P. et al., "A study of the interface between a fibrous polyurethan arterial prosthesis and natural tissue," *J. Bio. Mat. Res.*, 1982, vol. 16, pp. 827–838.

Barber, J. C. et al., "The acceptance of vitreous carbon alloplastic material, Proplast, in the rabbit eye," *Inv. Ophthal. Vis. Sci.*, 1980, vol. 19, pp. 182–191.

Barnham, J. J. et al., "Keratoprosthesis: a long-term review," *British J. of Opthalmology*, 1983, vol. 67, pp. 468–474.

(List continued on next page.)

*Primary Examiner*—David Isabella
*Attorney, Agent, or Firm*—Fish & Richardson

[57] ABSTRACT

A corneal prosthesis including an optical element having an optically transparent central portion and an anterior surface capable of supporting a layer of epithelial cells, the optical element being made of optical material having water content between 50% and 90% and a tensile strength greater than 20 kg/cm², and a porous outer skirt secured to the periphery of said element, said skirt being sufficiently porous to permit cell ingrowth and tissue attachment. Also disclosed are methods of making, seeding and using corneal implants having epithelial layers thereon and porous implant material of a coherent mass of randomly oriented fibers having an interconnected network of pores.

19 Claims, 3 Drawing Sheets

OTHER PUBLICATIONS

Bobyn, J. D. et al., "Effect of pore size on the peel strength of attachment of fibrous tissue to porous–surfaced implants," *J. Biomed. Mat. Res.*, 1982, vol. 16, pp. 571–534.

Cardona, H., "Prosthokeratoplasty," *Cornea*, 1983, vol. 2, pp. 179–183.

Civerchia–Perez, L. et al., "Use of collagen–hydroxyethylmethacrylate hydrogels for cell growth," *Proc. Natl. Acad. Sci. USA*, 1980, vol. 77, No. 4, pp. 2064–2068.

Dohlman et al., "Synthetic Polymers in Corneal Surgery," *Arch. Ophthalmology*, 1967, vol. 77, pp. 252–257.

Dunn, M. W. et al., "Collagen Membrances in Experimental Corneal Surgery," Ophthalmology Surgery, 19871, vol. 2, p. 9–11.

Gangjee T. et al., "Species Related Differences in Percutaneous Wound Healing," *Ann. Biomed. Eng.*, 1985, vol. 13, pp. 451–467.

Gipson, I. K. et al., "Hemidesomosome formation in vitro," *J. Cell. Bio.*, 1983 vol. 97, pp. 849–857.

Kresina, T. F. et al., "Isolation and Characterization of Basement Membrane Collagen from Huma Placental Tissue: Evidence for the Presence of Two Genetically Distinct Collagen Chains," *Biochemistry*, 1979, vol. 18, pp. 3089–3097.

Lamberts, S. C. et al., "A new Aloplastic Material for Ophthalmic Surgery," *Ophthalmic Surgery*, 1978, vol. 9, pp. 35–42.

Leiderner, J. et al., "A Novel process for the manufacturing of porous grafts: Process description and product evaluation," *J. Biomedical Materials Research*, 1983, vol. 17, pp. 229–247.

Jumblatt, M. M. et al., "–Adrenegic and Serotonergic Responsiveness of Rabbitt Corneal Epithelial Cells in Culture," *Inv. Optal. and Vis. Sci.*, 1983, vol. 24, pp. 1139–1143.

NIH grant application entitled "Development of Functional Biopolymers for the Eye," *submitted by Boston University Medical School to NIH and dated Jan. 22, 1981*.

Ofstead, R. F. and Poser, C. J., "Semicrystalline Poly (vinyl alcohol) Hydrogels: Synthesis and Characterization," *Proc. of the ACS Div. Polym. Mat.*, 1987, vol. 57, pp. 361–365.

Poser, C. J. and Ofstead R. F., "Semicrystalline Poly (vinyl alcohol) Hydrogels: Structure and Properties," *Proc. of the ACS Div. Polym. Mat.*, 1987, vol. 57, pp. 366–370.

Sendele, D. D. et al., "Intracorneal Lens Implantation," *Arch. Ophthalmology*, 1988, vol. 101, pp. 940–944.

Spector, M. et al., "Characteristics of Tissue Growth into Proplast and Porous Poyethylene Implants in Bone," *J. Biomed. Mat. Res.*, 1979, vol. 13, pp. 677–692.

Sugrue, S. P. et al., "Response of Basal Epithial Cell Surface and Cytoskeleton to Stabilized Extracellular Matrix Moleculars,", *J. Cell Bio.*, 1981, vol. 91, pp. 45–54.

Trinkaus–Randall et al., "A technique for Obtaining Corneal Epithelial Cells," *Inv. Ophthal. and Vis. Sci.*, 1985, vol. 26, pp. 233–237.

Trinkaus—Randall, V. and Gipson, I., "Role of Calcium and Calmodulin in Hemidesmosome Formation In Vitro", *J. Cell. Bio.*, 1984, vol. 98, pp. 1565–1571.

Vandersteenhoven, J. J. et al., "Osteoinduction within porous polysulfone implants at extraosseous sites using demineralized allogenic bone matrix," J. Biomed. Mat. Res., 1983, vol. 17, pp. 793–806.

von Recum, A. et al. "Permanent Percutaneous Devices," *CRC Crit. Rev. Bioeng.*, 1981, vol. 11, pp. 37–77.

Yamada, H. (F. G. Evans, ed.) "Strength of Biological Material," (Williams & Wilkins, Baltimore), 1970, pp. 219–247.

5,489,300

SURGICAL METHOD FOR IMPLANTING A CORNEAL IMPLANT

This is a continuation of application Ser. No. 07/783,618, filed Oct. 25, 1991, now abandoned, which is a divisional of 07/163,383 filed Mar. 2, 1988, now U.S. Pat. No. 5,108,428.

BACKGROUND OF THE INVENTION

The invention relates to the structure, manufacture and use of synthetic implants, e.g., a corneal prosthesis.

A synthetic implant is a synthetic material member incorporated into a living body, typically replacing or assisting a failing living component. To be successful it must serve its intended purpose and not be rejected by the receiving body or otherwise have unacceptable side effects.

A corneal prosthesis, often referred to as a keratoprosthesis, replaces part or all of the cornea, typically when the cornea has been damaged so as to cease serving the function of an optically transparent window to the retina. A complication to be avoided with a corneal prosthesis is extrusion of the prosthesis from the eye when epithelial tissue grows in behind the prosthesis.

Two types of corneal prostheses employ a threaded optical element (e.g., methyl methacrylate). In one, typically referred to as a stromal or intralamellar fixated keratoprosthesis, a threaded ring portion is embedded in the cornea, and a threaded optical shaft passes through it. In the second, typically referred to as a nut and bolt design, a threaded optical shaft has a mushroom-shaped cap, and a threaded "nut" is placed behind the cornea. Examples are described in Barnham, J. J., et al., "Keratoprosthesis: a long-term review", *British J. of Ophthalmology,* 1983, Vol. 67, pp. 468–474; Cardona, H., "Prosthokeratoplasty", *Cornea,* 1983, Vol. 2, pp. 179–183; Peyman U.S. Pat. No. 4,470,159; and Binder U.S. Pat. No. 4,586,929. Cardona describes securing Dacron mesh covered with autologous tissue to the ring to promote tissue ingrowth to retain the prosthesis. Binder discloses using hydrogel material having a water content between 30% and 79% for the ring and possibly also the optical cylinder, reporting avoidance of extrusion of the hydrogel material from the eyes.

Some other corneal prostheses are disclosed in White U.S. Pat. No. 4,612,012; Kelman U.S. Pat. No. 4,563,779 and Kern U.S. Pat. No. 4,676,790. The White prosthesis employs a centrally lenticular disc adhesively secured to a ring having an outer tissue contacting surface of a biologically compatible material. Kelman discloses removing a corneal plug from an eye, boring from the posterior surface toward the anterior surface but leaving the Bowman's lamina and epithelial layer intact, providing an optically clear plug in the bore, and returning the corneal plug to the eye. Kern discloses making a recess partially into the cornea, and bonding in the recess a shaped lens of cross-linked collagen or collagen-like material; the anterior surface has a protein condensate (formed, e.g., during laser shaping of a lens blank) that simulates a Bowman's lamina and permits growth of epithelial cells over the top of the lens implant.

SUMMARY OF THE INVENTION

In one aspect the invention features in general a corneal prosthesis that includes an optical element and a porous outer skirt secured to the periphery of the element. The optical element has an optically transparent central portion and an anterior surface that is capable of supporting a layer of epithelial cells and is made of optical material having a water content between 50% and 90% in order to provide diffusion of nutrients through the prosthesis to the epithelial cells and a tensile strength greater than 20 kg/cm$^2$ in order to provide sufficient prosthesis strength during surgical implantation and use. The outer skirt is used to secure the optical element to the patient's surrounding tissue and is sufficiently porous to permit cell ingrowth and tissue attachment.

In preferred embodiments, the optical element is made of a polyvinyl alcohol copolymer hydrogel system (most preferably one prepared from a polyvinyltrifluoroacetate precursor copolymer including vinyl acetate or maleic anhydride as the comonomer) or a polyvinylpyrrolidone blend (most preferably with polysulfone or cellulose acetate); the optical material has between 65% and 80% water content, a tensile strength greater than 40 kg/cm$^2$, an elongation greater than 100%, and a modulus of elasticity greater than 3 kg/cm$^2$; the outer skirt is made of a coherent mass of melt drawn fibers having an interconnecting network of pores; and the fibers are made of a polyolefin material.

In another aspect the invention features an implantable ophthalmic prosthesis including an optically transparent portion and a layer of epithelial cells covering the anterior surface of the optical element. The optical element is made of material having a water content between 50% and 90% and a tensile strength greater than 20 kg/cm$^2$.

In another aspect the invention features in general a method of making a corneal prosthesis by bonding a porous outer skirt to the periphery of an optical element having an optically transparent central portion and an anterior surface capable of supporting a layer of epithelial cells. Preferably, the optical material has water content between 50% and 90% and a tensile strength greater than 20 kg/cm$^2$; the skirt is made by melt-blowing thermoplastic fibers to obtain a coherent mass of fibers having an interconnected network of pores; the optical element and porous skirt are bonded together by solvent welding involving dipping the skirt in a solvent (one which is a solvent for the optical element polymer and a nonsolvent for the porous skirt polymer) and applying pressure between it and the optical element; and the optical element is obtained by solvolysis of a precursor of the element, and the bonding involves solvent welding the precursor prior to solvolysis.

In another aspect our invention features in general a corneal prosthesis implant method in which the optical element can be implanted with or without prior seeding of corneal epithelial cells on the anterior surface. The anterior surface can be coated or laminated prior to or after implanting with a basement membrane component(s) (most likely protein) to facilitate growth of epithelial cells on it. The surgical implanting can involve suturing, application of a biological adhesive, or both. When cells are seeded onto the anterior surface prior to implanting, they preferably are autologous cells obtained from the patient and cultured prior to seeding; likewise, there is migration of seeded epithelial cells out from the anterior surface of the optical element to the surrounding host tissue and of the patient's epithelial cells from the host surrounding tissue to the anterior surface. The prosthesis preferably has a porous outer skirt which is sutured to the surrounding tissues; there may or may not be seeding of autologous stromal keratocytes on and into the porous skirt before implanting; there is migration of the stromal keratocytes from surrounding tissue into the pores after implanting; and, prior to implanting, a compound which selectively retards epithelial downgrowth and extrusion, thus preventing future rejection while permitting stromal keratocyte ingrowth is applied to the skirt.

In a further aspect our invention features, in general, preparing a corneal prosthesis for implanting by seeding epithelial cells on the anterior surface of an optical element. Preferably, the anterior surface is coated either by adsorption or chemical attachment or integration during polymerization with basement membrane component(s) (most likely protein) prior to seeding; the seeding involves providing a nutrient medium to the cells while the cells increase in number; there also is a porous outer skirt attached to the optical element and it is optionally seeded with stromal keratocytes simultaneously with seeding of the epithelial cells so that both the epithelial cells and stromal keratocytes are provided with a nutrient medium simultaneously and are increasing in number.

In yet a further aspect our invention features an implant made of a coherent mass of melt blown fibers. The majority of fibers are between 2 and 20 microns in diameter. The mass has an interconnected network of pores, and the void volume is greater than 40% in order to facilitate tissue ingrowth. Preferably, the majority of pores are between 10 and 100 microns; the fibers are made of polyolefin material; and the implant includes a member of different material secured to said mass.

Other features and advantages of the invention will be apparent from the following description of a preferred embodiment thereof and from the claims.

DESCRIPTION OF THE PREFERRED EMBODIMENTS OF THE INVENTION

The preferred embodiments of the invention will now be described.

Drawings

STRUCTURE, MANUFACTURE, AND USE

Figure 1:
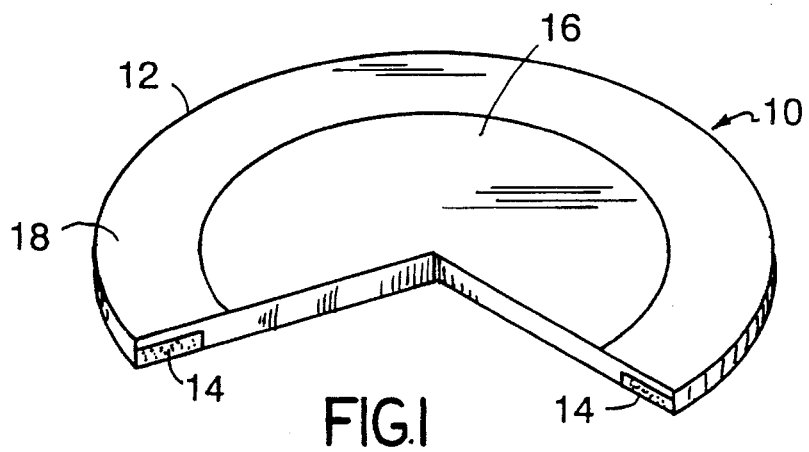
FIG. 1 is a diagrammatic perspective view, partially broken away, of a corneal prosthesis according to the invention.

Referring to FIG. 1, there is shown corneal prosthesis 10 including optical element 12 and porous outer skirt 14. Optical element 12 includes a full-depth optically-transparent central portion 16 and a thinner outer portion 18 that overlies skirt 14, which extends around the periphery of prosthesis 10.

Optical Element

Optical element 16 is made of an optically transparent hydrogel material having a water content between 50% and 90%, a tensile strength of greater than 20 kg/cm² and an anterior surface capable of supporting a layer of epithelial cells. The water content of the material is related to the permeability of the material to nutrients and metabolites and thus is related to the ability of the material to permit transfer to the epithelial layer living thereon in use. The tensile strength is related to the ability of the material to resist stresses to which the material is subjected at the anterior segment of the eye and stresses to which the material is subjected during surgical implantation. The tensile strength of the human cornea typically is in the 30–40 kg/cm² range, and it is desirable to have the material strength not too much below that of the human cornea and preferably above the strength of the human cornea (e.g., above 40 kg/cm²). The anterior surface must be able to support a layer of epithelial cells thereon so as to completely cover the anterior surface in order to decrease the potential for epithelial downgrowth and resulting extrusion; the continuous epithelial layer also provides an effective barrier to microorganisms and permits development of a normal tear film when implanted. The material, as is preferred for implant materials generally, also does not induce inflammation and resists enzymatic degradation. Related to optical transparency of the material is the ability to process the material into desired shape (preferably using conventional plastic processing techniques including molding and lathe cutting) to provide appropriate optical power to form a high quality image at or near the retina.

The material of optical element 16 preferably is a hydrogel, e.g., made of a polyvinyl alcohol copolymer system, as described in Ofstead U.S. Pat. No. 4,618,649 ("Ofstead '649") and Ofstead U.S. Pat. No. 4,528,325 (Ofstead '325), or of a polyvinylpyrrolidone blend, as described in Ofstead European Published Patent Application No. 0137686A ("Ofstead '686A"). The presently most preferred material is polyvinyl-alcohol-co-vinyl acetate 97.6:2.4 mole percent (prepared from a copolymer of vinyltrifluoroacetate and vinyl acetate) made according to the methods described in Ofstead '649 (Example 8). This material is a semi-crystalline hydrogel, has an equilibrium water content of 73% in normal saline, tensile strength of 110 kg/cm², initial modulus of elasticity of 10–15 kg/cm, and elongation of 436%. Tensile strength, elongation and modulus were all measured as described at col. 6, line 57 to col. 7, line 4 of Ofstead '649. Examples of polyvinylpyrrolidone blends meeting the water content and strength criteria mentioned above are polyvinylpyrrolidone/polysulfone (an 80/20 blend having an equilibrium water content of 57% in normal saline, a tensile strength of 30 kg/cm² and elongation of 170%) and polyvinylpyrrolidone/cellulose acetate (a 50/50 blend having an equilibrium water content of 51% in normal saline, a tensile strength of 51 kg/cm², and elongation of 152%), both made according to methods described in Ofstead '686.

Other materials can be used so long as the water content is greater than 50% (preferably between 65% and 80%) and the tensile strength is greater than 20 kg/cm² (preferably greater than 40 kg/cm²). Further strength-related criteria that preferably are met are a modulus of elasticity between 3 and 115 kg/cm² (preferably 5–15 kg/cm²), and elongation between 100–1000% (preferably greater than 150%). Other candidate materials for optical element 12 include: other polyvinyl alcohol copolymers, e.g., containing vinyl acetate (0–5%) or maleic anhydride (0–3%) (mole percent) as the comonomer, other hydrogel materials described in Ofstead '649 (see discussion at col. 3, lines 19–50 in particular), Ofstead '325, Ofstead '686A (including other blends with polyvinylpyrrolidone) and Hammar et al. U.S. Pat. No. 4,673,539, all of which are hereby incorporated by reference. In the hydrogel materials, the water content and strength properties can be altered by varying the comonomer type and content in the polymer systems or the material ratios in the blends, permitting tailoring to meet the criteria described above and to optimize the material.

The presently most preferred polyvinyl alcohol-co-vinyl acetate material described above is made by molding of solvent cast discs of the precursor polymer as described in Ofstead '649, although lathe processing of thermally-molded buttons or UV polymerized buttons can also be used. Some initial studies indicate possible better epithelial growth (as described below) when using materials made by bulk UV-polymerization, also described in Ofstead '649.

Porous Skirt

Figure 4:
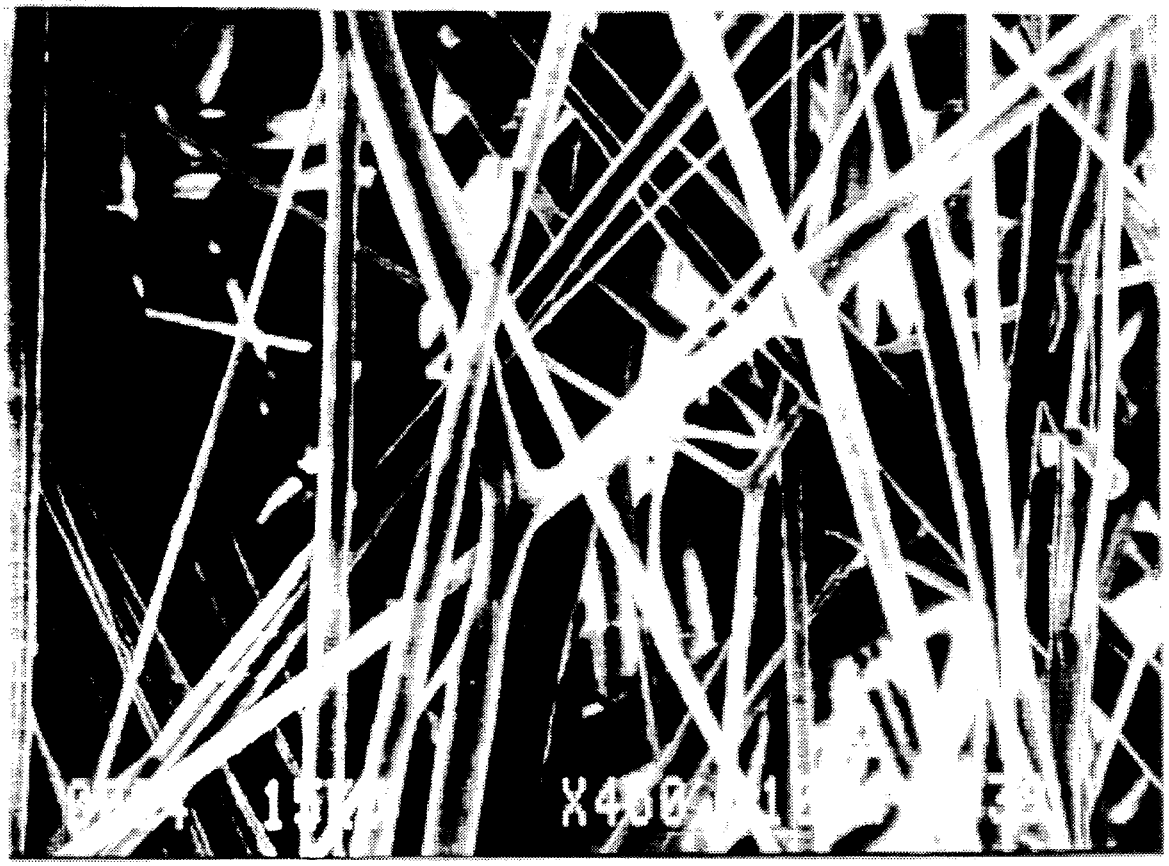
FIG. 4 is a scanning electron micrograph showing the structure of the material of a porous outer ring of the FIG. 1 prosthesis.

Porous outer skirt 14 is preferably made of a coherent mass of melt blown fibers having an interconnected network of pores. The majority of fibers are preferably between 2 and 20 microns in diameter. The void volume (related to both size and spacing of fibers) of the preferred skirt material ranges between 70% and 94% (% of total volume not occupied by fibers); it could be less than 70%, but should be above 40% (most preferably above 55%) to get adequate bonding to both the optical element and the surrounding tissue and to permit tissue ingrowth. The majority of pores are preferably between 10 and 100 microns, as is shown in FIG. 4. Pore size can be determined directly by measurements of scanning electron micrographs, taking measurements between fibers that appear to be in the same or in nearby planes. The size and spacing of fibers are important in that the spacing between fibers must be sufficient for the cells to migrate into the material and occupy the voids, there must be sufficient room for capillary ingrowth, the fibers must have a minimum diameter for the cells to travel along them, the fibers should have a minimum size to provide desired strength to the skirt without reducing pore size, and the fibers should not be so large as to take up too much volume.

The melt blown fiber construction permits obtaining fibers that have the desired small diameters, spacing, and sufficient bonding to each other to provide sufficient strength to resist stresses to which the skirt is subjected during suturing and implantation. The bonding between fibers also avoids creation of large holes or tears at sutures. The melt blown fiber construction also provides good interconnection of the pores throughout the web. The porous material encourages stromal keratocyte ingrowth, resulting in permanent stromal wound apposition so that prosthesis 10 heals securely in place.

The presently most preferred materials for porous skirt 14 are polybutylene (e.g., available under the trade designation Shell 8010) or a polybutylene/polypropylene blend (80%/20%). Other materials that can be used include other polyolefins such as polyethylene, polyethylene/polybutylene blends, polypropylene (e.g., available from Himont under the Profax 973 or D19A trade designations) polybutylene/polypropylene blends (e.g., an 80/20 blend) and other biocompatible plastics. Polyurethane should be useful if components deleterious to ingrowing tissue are removed. Also, the porous outer skirt could be made of other porous structures permitting tissue ingrowth, particularly coherent masses of fibers made by other melt and draw procedures such as procedures employing electrical field to draw molten extruded fibers so as to greatly reduce their diameters before collecting them on a belt. By "melt drawn fibers" herein we mean fibers prepared by melting, extruding through orifices, and reducing the diameters of the fibers by drawing them, e.g., by blowing air past them or by an electrical field. The plastic selected, like all implant material, should not induce corneal inflammation and should resist enzymatic degradation.

Figure 4A:
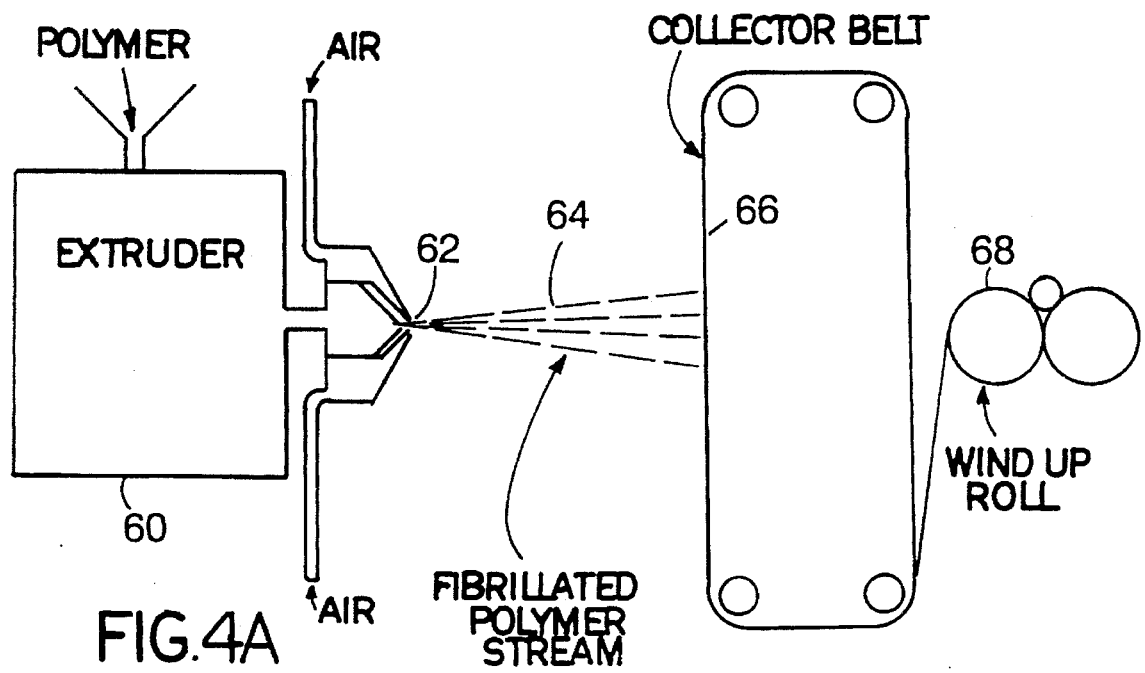
FIG. 4A is a diagram of a melt blown fiber process used in manufacturing the porous material of the outer skirt.

Referring to FIG. 4A, the microfiber web is made by extruding the plastic at extruder 60 through a series of small apertures 62 formed by clamped saw-tooth edges or drill holes, subjecting the extruded plastic to converging air jets at slight angles to the direction of extrusion on both sides to cause attenuation and elongation of extruded molten fibers 64, collecting fibers 64 on a moving belt 66, and removing the web at wind-up roll 68, according to techniques well known in the art, as generally described, e.g., in Hauser U.S. Pat. No. 4,118,531, which is hereby incorporated by reference. (A chamber including a second set of air jets at its entrance can also be placed to direct the fibers to the moving collecting belt, as described in Example 11 herein.) The fibers become entangled and also become bonded to each other during the process so as to form a coherent mass, as shown in the electron micrograph of FIG. 4. The microfiber web is cut into the desired ring shape of porous outer skirt 14. The melt-blown fiber method is useful because porosity is controllable by factors which control web density and fiber size (e.g., air temperature, air flow rate, polymer extrusion rate, collector speed, distance of collector from the extruder). Porosity can thus be varied to obtain optimum tissue ingrowth and viability along with desired strength and flexibility of the material. The speed of the belt can also be varied to control the thickness of the web. Other advantages of the melt blown fiber technique are that the nonwoven web is directly formed, a variety of polymers can be processed, and good fiber-fiber bonding can be achieved without the use of a bonding agent. Example 11 hereto describes preparation of a melt blown fiber web according to the invention.

Manufacture of Two-Piece Prosthesis

In manufacture, the precursor of optical element 12 (prior to the solvolysis step, described in Ofstead '649, which step causes water-swelling) is formed to shape (either by molding or by lathing of a preformed button) and solvent welded to the porous outer skirt 14 by dipping skirt 14 in acetone and pressing the two together 12. Acetone is a solvent for the polymer of the optical element and a nonsolvent for the polybutylene skirt material. Just enough pressure is applied to make good contact between the two components. The precursor of element 12 is then taken through the solvolysis stage attached to skirt 14, optical element 12 retaining its shape and optical clarity.

Skirt 14 is sufficiently elastic to accommodate changes in the shape of optical element 12 during the solvolysis stage. A benefit of solvent welding is obtaining mechanical interlocking of the fibers in the hydrogel, avoiding the problem of delamination at an adhesive interface. This is especially important with a material which is going to change in size on solvolysis and swelling. Also, by avoiding the use of adhesive to bond the two together, the different materials interfacing with the human eye are limited in number. This attachment method also avoids subjecting the hydrogel to processes that might potentially change its properties.

Prosthesis Seeding Device

Figure 5:
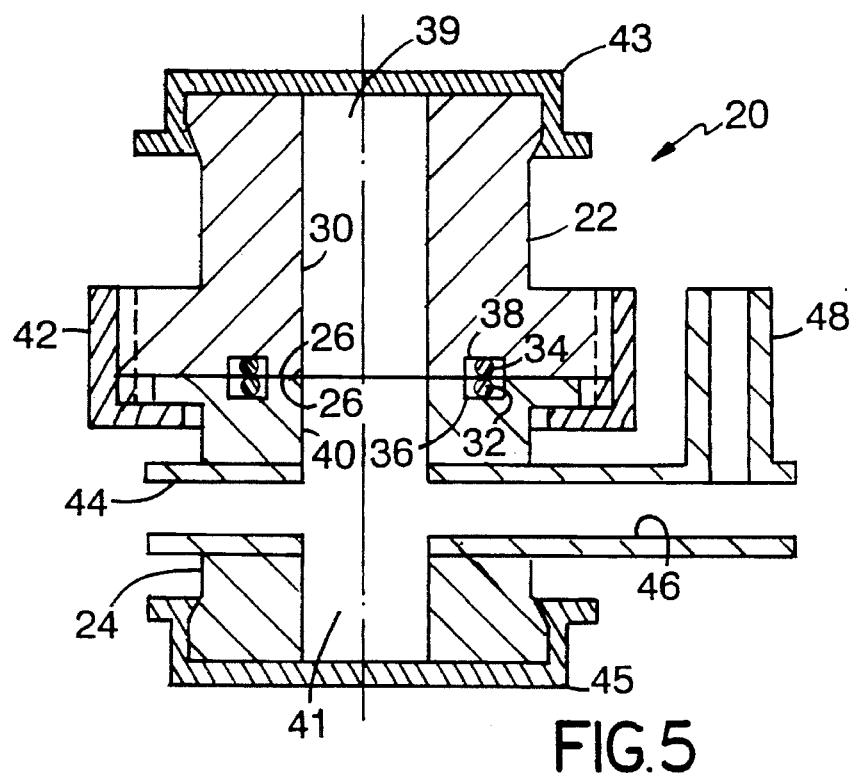
FIG. 5 is a diagrammatic vertical sectional view of a holder used to seed the FIG. 1 prosthesis.

Referring to FIG. 5, there is shown holding device 20 used for holding prosthesis 10 while seeding different cells on different surfaces of corneal prosthesis 10. Upper and lower housings 22, 24 mate at flat surfaces 26, 28, in which are provided opposing annular recesses 30, 32, retaining opposing O-rings 34, 36 therein. Housing 22 has a cylindrical bore 38 to provide a first seeding chamber 39, and housing 24 similarly has cylindrical bore 40 to provide a second seeding chamber 41. Housings 22, 24 are secured together by threaded collar 42, and are sealed closed at their respective ends by snap-on caps 43, 45. Lower housing 24 has ports 44, 46, the latter communicating with an upwardly directed tube 48.

Seeding of Prosthesis

Prior to implantation of prosthesis 10 in the patient's eye, holding device 20 can be used to seed the anterior surface of optical element 12 with epithelial cells and porous skirt 14 with stromal keratocytes. The completed prosthesis 10, shown in FIG. 1, has an outer diameter equal to that of bores 38, 40. Prior to seeding, prosthesis 10 initially has a skirt 14 and overlying portion 18 that extend beyond the bore diameters to slightly more than the diameter of O-rings 34, 36 so that the upper surface of completed prosthesis 10 is sealed from the lower surface. The oversized prosthesis is sealed between O-rings 34, 36, with the anterior surface forming second seeding chamber 41 with bore 40 and the posterior surface forming first seeding chamber 39 with bore 38. Device 20 is filled with culture medium in chamber 39 in bore 38, sealed closed, and placed in a position inverted from that of FIG. 5, and culture medium with epithelial cells is added to chamber 41. After epithelial cell attachment to the anterior surface of optical element 12, chamber 40 is sealed; device 20 is inverted to the position of FIG. 5; and stromal keratocytes are added to chamber 38. The cell culturing and seeding methodologies described in the examples below are applicable to seeding in holder 20. Prior to seeding, both optical element 12 and porous skirt 14 can optionally be coated with a basement membrane component to facilitate attachment and healing when implanted; one or more of the following could be used: laminin, fibronectin, Type I collagen, Type IV collagen or a cell-free extract prepared from the extracellular matrix of corneal epithelial cells. The coating can involve adsorption, chemical attachment or integration during polymerization.

During seeding of the porous skirt, culture medium can be flushed through ports 44, 46 to maintain the epithelial cells. Tube 48 maintains the liquid level in chamber 41 so that the nutrient medium is in contact with the prosthesis. The first seeding chamber 39 in bore 38 might additionally be provided with a cylindrical barrier (not shown) to keep the stromal keratocytes at the porous outer skirt only and away from the posterior surface of central portion 16. After seeding has been completed, caps 43, 45 are removed, and prosthesis 10 and holding device 20 are transferred under sterile conditions to a sterile punch in which prosthesis 10 is cut from the seeded, oversized prosthesis. Device 20 advantageously prevents cross-contamination of the cell types, keeping the epithelium from populating the porous skirt, something which would lead to epithelial growth under the prosthesis and extrusion.

Implantation of Prosthesis

Figure 2:
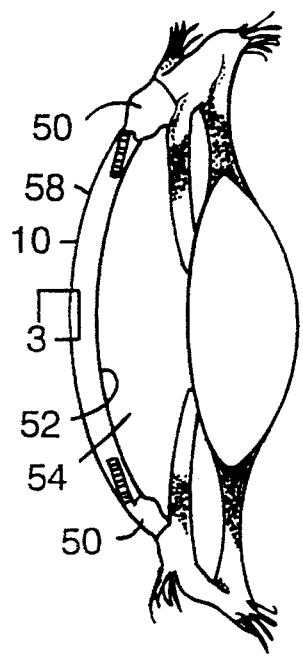
FIG. 2 is a diagrammatic sectional view of a portion of the human eye incorporating a corneal prosthesis according to the invention.
Figure 3:
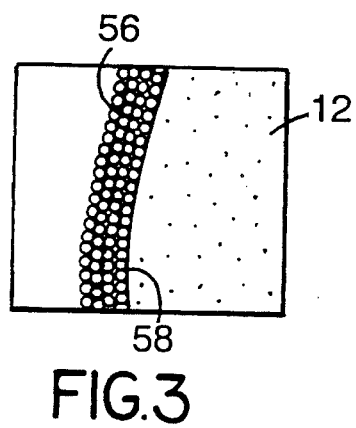
FIG. 3 is an enlarged view of a portion of FIG. 2 showing the anterior surface of the FIG. 1 prosthesis on which an epithelial layer has grown.

The prosthesis is surgically implanted in the eye employing known keratectomy procedures, for example, as described in the above-mentioned references. (See also the procedure described at the end of this section.) Referring to FIG. 2, the peripheral portion of prosthesis 10 including skirt 14 is sutured to cornea 50. Posterior surface 52 of prosthesis 10 seals anterior chamber 54, and the edge of overlying portion 18 is aligned with the epithelial layer of cornea 50, and skirt 14 is aligned with the stroma of the eye. Stromal tissue grows into the interconnected pores of porous skirt 14, serving to anchor prosthesis 10 in the patient's eye. Epithelial cells migrate from the epithelial layer of the surrounding tissue of cornea 50 to the anterior surface of optical element 12 and vice versa, forming a continuous epithelial layer 56 (see FIG. 3) on anterior surface 58 of element 12. Layer 56 desirably includes at least three cell layers and is about 50 to 100 um thick. The preseeding of the anterior surface with epithelial cells and the preseeding of the skirt with stromal keratocytes facilitates re-epithelialization and tissue ingrowth. The complete covering of the anterior surface provides a normal precorneal tear film and a barrier against microbial invasion.

Prior to surgically implanting prosthesis 10 in the human eye, porous outer skirt 14 can be treated with fibrin adhesive (available under the "Tissucol™" trade designation from Immuno GMBH, Vienna, Austria). (Another adhesive that can be used is polyphenolic protein bioadhesive available from Biopolymers, Inc., Farmington, Conn.). The fibrin adhesive retards epithelial cell growth into the region of the adhesive compared to the rate for the stromal keratocytes, permitting the stromal keratocytes to establish themselves in porous outer skirt 14 before the epithelial cells have a chance to migrate down and under the prosthesis and cause extrusion.

The materials employed have adequate strength to allow for initial suturing and to withstand the intraocular pressures without rupturing or leaking. The materials are compliant and generally have physical properties similar to those of the natural tissue surrounding the prosthesis, thereby avoiding such problems as pressure necrosis and fibrous encapsulation associated with stress concentration at the interface of two dissimilar materials.

A description of a penetrating keratoplasty procedure that is directed to laboratory experiments but includes applicable information follows. Recipient animals are anesthesized with intramuscularly administered ketamine/Rompun and topically administered proparacaine hydrochloride 0.5%. Heparin is also given intravenously in a dose of 1,000 units/kg body weight. A wire lid speculum is used to maintain the lids widely open and the nictitating membrane is excised. Superior and inferior rectus bridle sutures are placed and affixed to the drapes to stabilize the globe. A horizontal rectus muscle is grasped with toothed forceps, and, under direct visualization through an operating microscope, a partially perforating circular corneal incision is made with a trephine. The remainder of the full-thickness, circular corneal wound is completed with Castroviejo corneal scissors, and the recipient corneal button is removed. A peripheral iridectomy is performed with jeweler's forceps and Vannas scissors. If clotting of the aqueous humor is encountered, aqueous heparin (1000 units/ml) is slowly dripped into the anterior chamber through the trephine opening, using a 30 gauge irrigating cannula, while proceeding with surgery. (Heparin should be included in all irrigating solutions to prevent fibrin formation.) The keratoprosthetic material is initially anchored with four, cardinal, 10-0 nylon, interrupted sutures and then firmly secured with either a single running or multiple interrupted 10-0 nylon sutures and/or a biological adhesive. Gentamicin sulfate 0.3% ophthalmic solution is instilled at the completion of surgery.

Other Embodiments

Other embodiments of the invention are within the scope of the following claims.

Other methods could be used to bond the porous outer skirt to the optical element. E.g., the optical element could be taken through the solvolysis stage prior to bonding to the porous outer skirt.

The optical element could be formed to its desired shape when in the hydrogel state.

The melt blown material also has application in other implant devices and can be used to anchor members made of material that is different from the melt blown material.

The use of fibrin adhesive to inhibit epithelial downgrowth has application in other percutaneous type implants where epithelial downgrowth is a potential complication, e.g., peritoneal access devices, blood access devices, and periodontal surgery where there is a need to prevent the epithelium from migrating down the tooth-gingival interface.

Also, the surface properties of the hydrogels can be altered by introducing ionic functional groups and by chemically changing the distribution of these groups on the surface in order to influence the attachment and architecture of cells. E.g., Examples 9 and 10 herein describe a method of providing formation of amide acid and amide-amino acid groups in the hydrogel, some of which will thus appear at the surface. Initial studies indicate that there may be improved cell attachment and growth with these materials.

Features and advantages of this invention are further illustrated by the following examples, but the particular materials and amounts thereof recited in these examples, as well as other conditions and details, should not be construed to limit this invention.

EXAMPLE 1

Preparation of Epithelial Cell Culture

Corneal epithelial cells were removed and cultured using a modified version of Trinkaus-Randall, V. and Gipson, I. K., "A technique for obtaining corneal epithelial cells", *Inv. Ophthal. and Vis. Sci.,* 1985, Vol. 26, p. 233. New Zealand rabbits were sacrificed with 5 ml of sodium pentobarbital (325 mg) administered intravenously. The corneas were excised, the endothelium and Descemet's membrane were removed with forceps, and the remaining cornea (epithelium and stroma) was incubated in modified Dulbecco's Eagles medium containing 10 uM calcium (Gibco Lab., Grand Island, N.Y.) and 1.2 U/ml Dispase II (Boehringer Mannheim Lab, Indianapolis, Ind.) for one hour. The epithelial sheets were carefully teased from the stroma (Trinkaus-Randall and Gipson (1985); Gipson, I. K., et al., "Hemidesmosome formation in vitro", *J. Cell. Biol.,* 1983, Vol. 97, p. 849), and cultured in modified Dulbecco's medium 1:1 with Ham's F-12 nutrient medium in 35 mm diameter Falcon dishes (Jumblatt, M. M. and Neufeld, A., "B-adrenergic and seratonergic responsiveness of rabbit corneal epithelial cells in culture," *Inv. Ophthal. and Vis. Sci.,* 1983, Vol. 24, p. 1139). Once confluency was achieved, the primary cells were subcultured, and the cells from each 35 mm well were plated as described below.

EXAMPLE 2

Epithelial Cell Layer In Vitro

Corneal epithelial cells cultured according to Example 1 were seeded in vitro onto 1 cm diameter hydrogel discs of polyvinyl alcohol-co-vinyl acetate 97.6:2.4 mole percent (prepared from the copolymer of vinyltrifluoroacetate and vinyl acetate) as described above to study the ability to grow a continuous epithelial layer on the hydrogel that synthesized connective tissue proteins. The hydrogel discs were placed on tissue culture plates that were manufactured by a procedure that omitted usual treatments designed to promote cell growth, and discs were sterilized with an ultraviolet light for 2 hours. The cells were seeded onto plain or protein coated coated hydrogel discs at a density of $2 \times 10^4$ cells/disc. The protein coating involved adding one of the following protein solutions to the hydrogels for 45 min. at room temperature: laminin (0.5 mg/ml), fibronectin (0.2 mg/ml), Type I collagen (0.8 mg/ml), Type IV collagen (0.8 mg/ml) or a cell-free extract prepared from the extracellular matrix of corneal epithelial cells. The discs were then washed extensively with Puck's Saline G. The amount of adsorbed protein was determined by quantifying the protein before and after application. Only small amounts of protein actually adhered to the hydrogel as evidenced by the lack of significant change in concentration as determined by amino acid analysis. Laminin and fibronectin were obtained from Collaborative Research (Bedford, Mass.). Type I collagen was prepared from rat tail tendon and ultimately was fibrillar in structure. In contrast, Type IV collagen was obtained using a pepsin/acetic acid extraction of human placenta and exists in a degraded form (Kresina, T. F., and Miller, E. J., "Isolation and characterization of basement membrane collagen from human placental tissue: Evidence for the presence of two genetically distinct collagen chains," *Biochemistry,* 1979, Vol. 18, p. 3089). To prepare the cell free extract, corneal epithelial cells were cultured for a minimum of 6 weeks, the cells removed, and the cell layer washed and scraped, homogenized, and lyophilized. All assays were conducted on cells in first passage.

Cell Growth: Cell numbers were determined at days 2, 4, 6 and 8 using well known techniques. The number of corneal epithelial cells increased with time in culture for all surfaces. While there was a variation in plating efficiency among the different surfaces, the rate of cell growth was greater on hydrogels that had been coated with Types I or IV collagen than on hydrogels coated with fibronectin and laminin (seven population doublings versus six and four respectively).

Morphology: Cell morphology was monitored daily using a Nikon Diaphot phase contrast inverted microscope. After day 8, the tissue was fixed and processed for transmission election microscopy, and sections were examined using a Philips 300 microscope. Cell spreading occurred within the first 1.5 hr. on all surfaces. By day 8, confluency was achieved on all the coated surfaces, and the corneal epithelium cultured on the hydrogel discs was multilayered.

Protein Synthesis: Collagen synthesis and accumulation was monitored by known techniques as a function of culture time to study the ability of the epithelial cell layer to synthesize basement membrane proteins, a requirement of a healthy, living cell. Collagen synthesis and accumulation was demonstrated on all surfaces and was found to be enhanced by coating with proteins.

EXAMPLE 3

Epithelial Cell Layer In Vivo

Hydrogel discs coated with Type I collagen and seeded with $2 \times 10^4$ epithelial cells in vitro as described in Example 2 were tested in vivo to study the ability to obtain a continuous corneal epithelial layer. Rabbits were anesthetized with 5 mg/kg xylazine and 35 mg/kg ketamine administered intramuscularly. When needed, an additional half dose was administered. The rabbit corneal epithelium was removed with a scalpel, the nictitating membrane was excised, and a deep lamellar keratectomy 5 mm in diameter was performed. Discs which had been cultured until near confluency were placed into the keratectomy bed and secured with both interrupted and continuous sutures (10-0) (Alcon Surgical, Ft. Worth, Tex.). The eyelids were not sutured shut or covered, and antibiotics were administered daily.

To assess cell proliferation and migration of host and donor cells, radioactive markers were added either before or after transplantation. Three experimental protocols were conducted as described below: (1) Discs with or without cells were labeled for 10 hr. with $^3$H-thymidine on days 2, 4 and 6 after transplantation. This was accomplished by manipulating so that the cornea was bathed in the topically applied isotope. (2) Discs with a confluent layer of cells were labeled in vitro with $^3$H-thymidine for 18 hr. prior to transplantation and incorporation was examined on day 2, 4 and 6. (3) Discs with a confluent layer of cells were labeled in vitro with $^3$H-proline for 18 hr. prior to transplantation while the cornea was labeled in situ with $^3$H-thymidine for 18 hr. using an intrastromal injection prior to implantation of the disc. Migration of epithelial cells was examined on days 2 and 4.

In the first series (where both the discs and surrounding host cornea were labeled in vivo), it was observed that for the preseeded discs, the total number of cells on the central disc increased with time while the total number of cells in the peripheral rim of the surrounding host cornea decreased with time. For the unseeded discs, 99% of the total counts were found in the peripheral rim on days 2, 4 and 6. These results indicate that epithelial cell proliferation occurred on preseeded discs.

In the second series (where the discs were labeled in vitro before transplanting), there was an increase of counts in the peripheral rim of host cornea and a decrease in counts on the hydrogel discs, indicating that cells migrated off the central disc onto the peripheral rim of host cornea.

In the third series (where the discs and host tissue were labeled with different markers) there were substantial counts of the preseeded cells on the peripheral rim of the host cornea and of the host cells on the disc on day 6, indicating migration of preseeded cells onto the host tissue and of host cornea epithelial cells onto the disc.

EXAMPLE 4

Preparation of Stromal Keratocytes

Stromal keratocytes were cultured for use in seeding melt blown fiber samples. The corneas were excised, and the epithelium and endothelium were removed as described in Example 1 above. The stroma were cut into pieces (0.5 mm×0.5 mm) and placed into T25 Falcon Tissue Culture flasks. The flasks contained Dulbecco's medium and Ham's nutrient medium 1:1 with the following additions: 1% nonessential amino acids, 1% penicillin/streptomycin, 1% sodium pyruvate, 10% fetal bovine serum. The explants were not disturbed for one week and thereafter fed twice a week. Cells for experiments were removed once the explants had grown out.

EXAMPLE 5

Stromal Keratocyte Ingrowth In Vitro

Stromal keratocyte cells cultured as in Example 4 were seeded onto 6 mm diameter blown microfiber discs (made of polybutylene or polypropylene or a blend of polypropylene and polybutylene and made as described above) that had previously been sterilized under ultraviolet light for 2 hrs., and coated with Type 1 collagen as in Example 2. This was done by placing the discs on sterile filters to which the cells did not adhere (MILLICELL HA, 0.45 um; from Millipore, Bedford, Mass.). 5×10$^4$ cells/per disc were seeded onto each disc in a volume of 50 µl. Medium (as described in Example 4) was added to the well of a 24 well tissue culture dish and to the melt blown fiber disc.

Cell proliferation (i.e., an increase in numbers of cells with time) and collagen synthesis of the stromal keratocyte cells growing in and on the melt blown fiber discs were observed.

EXAMPLE 6

Stromal Keratocyte Ingrowth In Vivo

Blown microfiber discs coated with Type I Collagen and seeded with stromal keratocyte cells as in Example 5 were tested in vivo to study ingrowth of host tissue to anchor the material to the host tissue. The host keratocytes were labeled with a radioactive marker, and the melt blown fiber discs were implanted, using the methodology of Example 3. It was observed that numbers of labeled host cells counted in the discs increased with time, indicating ingrowth.

EXAMPLE 7

Combined Melt Blown Fiber and Hydrogel In Vitro

Melt blown microfiber discs to which layers of polyvinyl alcohol copolymer hydrogel (as described above) were laminated on the anterior surfaces were seeded with stromal keratocytes in the microfiber disc portions and implanted after radiolabeling of the host tissue, using the methodology of the previous examples. It was observed that labeled host cells migrated into the melt blown fiber material with time and that an epithelial layer grew over the anterior surface and only slightly downward at the edge.

EXAMPLE 8

Fibrin Adhesive

To study the ability of fibrin adhesive to inhibit epithelial growth vis-a-vis stromal keratocyte growth, tissue culture plates were divided into two regions by a strip of human fibrin adhesive (available under the Tissucol™ trade designation from Immuno GMBH, Vienna, Austria) and either epithelial cells (Example 1) or stromal keratocytes (Example 4) were placed on one side of the strip while the other side was left vacant. It was observed that stromal keratocytes were able to easily migrate across the strip while the epithelial cells were severely inhibited.

EXAMPLE 9

Preparation of Polyvinyltrifluoroacetate-co-maleic Anhydride

A mixture of 79.23 g. vinyltrifluoroacetate and 0.0245 g. maleic anhydride was placed in a polypropylene bag and 0.04 g. Darocure 1173 (E. Merck) added. The solution was purged of oxygen by bubbling $N_2$ gas through for several minutes and the bag was then sealed. The reaction was cooled in an ice water bath and polymerization was initiated by placing the mixture under a UV light source (RUL 3500

A fluorescent bulb, Southern New England Ultraviolet Co.) at a distance of four inches for 0.5 hours. The polymer was dissolved in acetone and precipitated from heptane to remove residual monomer and low molecular weight impurities.

EXAMPLE 10

Conversion to Hydrogels Containing Various Ionic Functional Groups

Polymer films or shaped articles such as those derived from Example 9 of polyvinyltrifluoroacetate-co-maleic anhydride were converted to hydrdogels by solvolyzing them either in 10% (v/v) $NH_4OH$ in MeOH or in 2% (v/v) ethylenediamine in MeOH. The solvolysis was run for two hours at room temperature followed by extraction in MeOH for two hours, also at room temperature. The former procedure results in the formation of an amide group and carboxylic acid group from each maleic anhydride group. The latter procedure results in the formation of a carboxylic acid group and an amide-amino group.

EXAMPLE 11

Preparation of Melt Blown Fiber Web

A blend of 80% Shell 8010 polybutylene and Exxon 3145 polypropylene pellets were fed to a ¾" Brabender extruder heated at 230° C. at the feed zone and increasing to 246° C. at the extrusion point. The polymer blend was extruded from a 10" wide die containing 0.017" holes (5 per inch). The extruded fibers were drawn by an air jet created by two air knives (pressure 22 psi, air temperature 250° C.) placed on either side of the die tip. The fibers were further drawn by passing the fiber stream through a 12"×12"×¾" chamber containing a second set of air knives (40 psi, ambient temperature) placed 1" in front of the extrusion die. The web was collected on aluminum foil against a drum placed 14" from the extrusion die. The rotation speed of the drum was adjusted to give a web of thickness=0.38 mm. basis weight= 45 gr/m² and void volume=87%.

We claim:

1. A surgical method of implanting a corneal prosthesis comprising providing a corneal prosthesis including an optical element having an optically transparent central portion and an anterior surface capable of supporting a layer of epithelial cells, said optical element being made of optical material having a water content between 50% and 90% and a tensile strength greater than 20 kg/cm², surgically implanting said prosthesis in a patient's eye, replacing part or all of the patient's cornea, and growing epithelial cells on said anterior surface only of said optical element so as to avoid extrusion, wherein said growing comprises seeding epithelial cells on said anterior surface prior to said implanting.

2. The method of claim 1 wherein said cells are autologous cells that have been obtained from said patient and have been cultured prior to said seeding.

3. The method of claim 1 wherein said growing comprises growing after said implanting, said growing further comprising migration of seeded epithelial cells out from said anterior surface to surrounding tissue of said patient and migration of epithelial cells from surrounding tissue of said patient to said anterior surface.

4. A surgical method of implanting a corneal prosthesis comprising providing a corneal prosthesis including an optical element having an optically transparent central portion and an anterior surface capable of supporting a layer of epithelial cells, said optical element being made of optical material having a water content between 50% and 90% and a tensile strength greater than 20 kg/cm², surgically implanting said prosthesis in a patient's eye, replacing part or all of the patient's cornea, and growing epithelial cells on said anterior surface only of said optical element so as to avoid extrusion, further comprising coating said anterior surface with one or more of lamin, fibronectin, Type I collagen, Type IV collagen, and a cell-free extract prepared from an extracellular matrix of corneal epithelial cells prior to said growing.

5. The method of claim 1 further comprising suturing after said surgically implanting.

6. The method of claim 5 wherein said providing comprises providing a porous outer skirt secured to the periphery of said element, said skirt having sufficient strength to resist tearing or stretching at suture holes.

7. A surgical method of implanting a corneal prosthesis comprising providing a corneal prosthesis including an optical element having an optically transparent central portion and an anterior surface capable of supporting a layer of epithelial cells, said optical element being made of optical material having a water content between 50% and 90% and a tensile strength greater than 20 kg/cm², surgically implanting said prosthesis in a patient's eye, replacing part or all of the patient's cornea, and growing epithelial cells on said anterior surface only of said optical element so as to avoid extrusion, wherein said providing comprises providing a porous outer skirt secured to the periphery of said element, said method further comprising growing stromal keratoctyes in pores of said outer skirt.

8. The method of claim 7 wherein said growing stromal keratocytes comprises seeding stromal keratocytes on and into said porous outer skirt prior to said implanting.

9. The method of claim 8 wherein said keratocytes are autologous cells that have been obtained from said patient and have been cultured prior to said seeding stromal keratocytes.

10. The method of claim 8 wherein said growing stromal keratocytes comprises growing after said implanting and further comprising migration of patient stromal keratocytes into said pores.

11. The method of claim 7 further comprising applying a basement membrane component to said skirt or to said patient's eye prior to said growing.

12. The method of claim 6 further comprising applying to said skirt a compound which selectively inhibits epithelial downgrowth while permitting stromal keratocyte ingrowth.

13. The method of claim 12 wherein said compound comprises fibrin adhesive.

14. The method of claim 12 wherein said compound comprises a proteinaceous material.

15. The method of claim 1 wherein said growing comprises growing after said implanting.

16. The method of claim 5 further comprising applying adhesive to said prosthesis before said surgically implanting.

17. The method of claim 7 wherein said growing stromal keratocytes comprises growing after said implanting.

18. The method of claim 8 wherein said growing stromal keratocytes comprises growing after said implanting.

19. The method of claim 6 wherein said porous outer skirt comprises a coherent mass of randomly-oriented melt drawn fibers having an interconnected network of pores.

* * * * *